(12) United States Patent
Dobbs (10) Patent No.: US 7,868,723 B2
(45) Date of Patent: Jan. 11, 2011

(54) POWER COUPLING DEVICE (75) Inventor: John Dobbs, Beverly, MA (US)

(73) Assignee: Analogic Corporation, Peabody, MA (US)

( * ) Notice: Subject to any disclaimer, the term of this patent is extended or adjusted under 35 U.S.C. 154(b) by 1495 days.

(21) Appl. No.: 10/787,270

(22) Filed: Feb. 26, 2004

(65) Prior Publication Data

US 2006/0022785 A1   Feb. 2, 2006

Related U.S. Application Data (60) Provisional application No. 60/450,038, filed on Feb. 26, 2003.

(51) Int. Cl.
H01F 27/32 (2006.01)
(52) U.S. Cl. .................................................. 336/84 C
(58) Field of Classification Search ............ 336/65, 336/83, 130–136, 84 R, 84 C
See application file for complete search history.

(56) References Cited

U.S. PATENT DOCUMENTS

| 3,336,662 | A | * | 8/1967 | Howland et al. ........... 29/602.1 |
| 4,145,591 | A | | 3/1979 | Takeda |
| 4,259,654 | A | | 3/1981 | Persson et al. |
| 4,293,884 | A | | 10/1981 | Schiller |
| 4,323,781 | A | | 4/1982 | Baumann et al. ............ 250/422 |
| 4,335,426 | A | | 6/1982 | Koizumi et al. |
| 4,496,202 | A | | 1/1985 | Beckmann et al. |
| 4,564,812 | A | | 1/1986 | Van Dijk |
| 4,725,781 | A | | 2/1988 | Roschmann |
| 4,785,246 | A | | 11/1988 | Sugimoto |
| 4,798,540 | A | | 1/1989 | Bernardi |
| 4,912,735 | A | | 3/1990 | Beer ........................... 378/15 |
| 5,105,095 | A | | 4/1992 | Rudy et al. |
| 5,191,309 | A | | 3/1993 | Laros |
| 5,296,810 | A | | 3/1994 | Morich |

(Continued)

FOREIGN PATENT DOCUMENTS

CA   20022434479 A1   10/2002

(Continued)

OTHER PUBLICATIONS

Crepaz et al. The Reduction of the External Electromagnetic Field Produced by Reactors and Inductors for Power Electronics, ICEM, 1986, pp. 419-423.

(Continued)

*Primary Examiner*—Tuyen T Nguyen
(74) *Attorney, Agent, or Firm*—McDermott Will & Emery LLP (57) ABSTRACT

A power coupling device for coupling power to a rotating member includes a primary magnetic core defining a first recess, and a secondary magnetic core defining a second recess and disposed adjacent the primary magnetic core. The primary and secondary cores are arranged so as to form an air gap therebetween. The air gap permits relative rotation of the cores about a common axis of rotation. A primary conductive winding is disposed within the first recess, and a secondary conductive winding is disposed within the second recess. At least one of the primary and secondary windings is a fractional turn winding, thereby enabling the transfer of power between multiple input and output voltages. Shielding is provided by a pair of continuous, circular, semi-toroidal shells arranged to support the currents needed to cancel the fields from the transformer.

27 Claims, 9 Drawing Sheets

U.S. PATENT DOCUMENTS

| | | | |
|---|---|---|---|
| 5,414,360 A | 5/1995 | Westphal et al. | |
| 5,499,281 A | 3/1996 | Weedon et al. | |
| 5,512,828 A | 4/1996 | Pausch et al. | |
| 5,530,425 A | 6/1996 | Harrison | |
| 5,570,073 A | 10/1996 | Muller | |
| 5,572,129 A | 11/1996 | Carlson | |
| 5,608,771 A | 3/1997 | Steigerwald et al. | 378/15 |
| 5,827,445 A | 10/1998 | Yoshida et al. | |
| 5,841,067 A | 11/1998 | Nakamura et al. | |
| 5,939,882 A | 8/1999 | Gebhardt et al. | |
| 5,986,531 A | 11/1999 | Carrozzi | |
| 6,058,000 A | 5/2000 | Koenck et al. | |
| 6,160,869 A | 12/2000 | Zapalac et al. | |
| 6,236,209 B1 | 5/2001 | Arz et al. | |
| 6,239,361 B1 | 5/2001 | Snaper | |
| 6,256,175 B1 | 7/2001 | Zhang | |
| 6,326,788 B1 | 12/2001 | Mulder et al. | |
| 6,346,816 B1 | 2/2002 | Damadian et al. | |
| 6,351,123 B1 | 2/2002 | Gebhardt | |
| 6,351,626 B1 | 2/2002 | Lohr | |
| 6,373,921 B1 | 4/2002 | Kliman et al. | |
| 6,407,470 B1 | 6/2002 | Seelig | |
| 6,437,571 B1 | 8/2002 | Danby et al. | |
| 6,448,500 B1 | 9/2002 | Hosaka et al. | |
| 6,469,508 B1 | 10/2002 | Damadian et al. | |
| 6,496,007 B1 | 12/2002 | Damadian et al. | |
| 6,501,016 B1 | 12/2002 | Sosnowski | |
| 6,576,877 B2 | 6/2003 | Dabelstein et al. | |
| 6,590,305 B2 | 7/2003 | Wang et al. | |
| 6,590,391 B1 | 7/2003 | Shudo et al. | |
| 6,590,953 B2 | 7/2003 | Suzuki et al. | |
| 6,617,852 B1 | 9/2003 | Danby et al. | |
| 6,636,406 B1 | 10/2003 | Anthony | |
| 6,653,924 B2 | 11/2003 | Vinciarelli et al. | |
| 6,687,108 B1 | 2/2004 | Anthony et al. | |
| 6,713,737 B1 | 3/2004 | Verhagen | |
| 6,762,088 B2 | 7/2004 | Acosta et al. | |
| 6,794,792 B2 | 9/2004 | Wang | |
| 6,839,401 B2 | 1/2005 | Nokita | |
| 2004/0000974 A1 | 1/2004 | Odenaal et al. | |
| 2006/0022785 A1 | 2/2006 | Dobbs | |
| 2006/0208727 A1 | 9/2006 | Matsumoto | |

FOREIGN PATENT DOCUMENTS

| | | | |
|---|---|---|---|
| GB | 0990418 B1 | | 4/1965 |
| JP | 01123406 A | * | 5/1989 |
| JP | 2211123 A1 | | 8/1990 |
| JP | 06181124 A | * | 6/1994 |
| JP | 08051039 A | * | 2/1996 |
| JP | 8335511 A1 | | 12/1996 |
| JP | 2003114203 A1 | | 4/2003 |
| JP | 2004166923 A1 | | 6/2004 |

OTHER PUBLICATIONS

Miyoshi et al. Reduction of Magnetic Flux Leakage From an Induction Heating Range, IEEE Transactions on Industry Applications, vol. 1A-19, No. 4, Jul./Aug. 1983.

Pedder et al. A Contactless Electrical Energy Transmission System, IEEE Transactions on Industrial Electronics, vol. 46, No. 1, Feb. 1999.

Williamson Labs, http://www.williamson-labs.com/480_shi.htm.

International Search Report and Written Opinion for corresponding PCT Application No. PCT/US08/52326.

* cited by examiner

POWER COUPLING DEVICE

CROSS REFERENCES TO RELATED APPLICATIONS

This application claims the benefit of priority under 35 U.S.C. §119(e) from co-pending, commonly owned U.S. provisional patent application Ser. No. 60/450,038, entitled "Non-Contacting Power Coupling Device," filed on Feb. 26, 2003.

FIELD OF THE INVENTION

The present invention relates to a power coupling device. More particularly, the present invention relates to a non-contacting power coupling device for coupling power to rotating systems, without using sliding contacts.

BACKGROUND

Systems that include rotating units require a power coupling device for coupling power to the electronic components within these rotating units. For example, when using CT scanners, it is necessary to supply power to the electronics on the rotating gantry, using a power coupling device. Traditionally, these power coupling devices have been slip-ring/brush assemblies. Slip-rings transfer electricity between a stationary member and a rotating member, through the contact of two materials, i.e. via a sliding contact. Slip-ring assemblies typically include two or more continuous conducting rings, and one or more brushes on each ring for delivering current to and from the rings.

Typically, numerous slip-rings must be used, in order to supply many different voltage levels, as required by the various electronic components of the rotating units. Conventional brush and slip-ring mechanisms tend to be dirty, unreliable, and noisy. Electric noise generation can cause interference with sensitive diagnostic procedures, such as CT imaging. Maintenance can be a significant problem, and the wearable components must be periodically replaced. These components can be converted to metallic dust, which may cause problems with ultra-sensitive electronics. Other drawbacks of slip-ring assemblies include the cost and complexity of manufacture, due to the special materials and the mechanical precision that are required.

A number of prior art references disclose inductive power coupling devices that allow power to be coupled to rotating systems, such as CT scanners, without using slip-rings. For example, U.S. Pat. No. 4,323,781 to Baumann discloses an inductive transformer for transmitting energy to the x-ray tube in a rotatable CT-scanning system. The inductive transformer in the Baumann patent consists of primary and secondary windings. An alternating current passing through the primary winding induces a current in the secondary winding. The primary winding is stationary with respect to the scanning system, whereas the secondary winding rotates with the scanning system, and provides power to the rotating x-ray tube.

U.S. Pat. No. 4,912,735 to Beer discloses a similar concept, namely a power transfer apparatus including two concentric rings mounted on a static member and a rotating member, respectively. The rings have opposed annular faces, each containing a groove. Conductive windings in each groove provide an inductive coupling means for coupling power to the rotating unit in the CT scanner. U.S. Pat. No. 5,608,771 to Steigerwald applies a substantially similar concept to a quasi-resonant high voltage generation scheme.

Although the devices discussed above allow for power transfer to rotating systems, without the need for sliding contacts and ensuing inconveniences, they suffer from a number of drawbacks. For example, these prior art devices do not provide to the user the flexibility of transferring power between a plurality of input and output voltages, as is necessary in many rotating systems such as CT scanners. For example, the user of a large CT system may need to derive many different voltages, at a relatively low power, for components on both the rotating and the stationary gantries of the CT system. However, the prior art power coupling devices discussed above do not provide such flexibility. Also, these prior art devices provide few options to the user for optimizing the current and voltage in the power transfer device, so as to achieve the best power transfer efficiency. Finally, none of these patents discuss the problem of shielding, which is a significant difference between inductively coupled systems and mechanical slip rings which are typically constant voltage devices.

For these reasons, there is a need for a more efficient power coupling device for rotating systems, which enables the user to transfer power between multiple voltages, as desired, and enables the user to optimize the current and voltage in the power coupling device, in order to achieve an optimum transfer efficiency. It is also desirable to provide an effective shielding mechanism.

SUMMARY

The present invention is directed to a non-contacting power coupling device that couples power between stationary and rotary components, without using sliding contacts. In particular, the present invention features the use of fractional turn windings, in order to provide flexibility in the choice of the input and output voltages in the power transfer system.

In one embodiment, the power coupling device of the present invention includes a primary magnetic core, and a second magnetic core disposed adjacent the primary core. The primary core defines a first recess or groove, and the secondary core defines a second recess, which is disposed opposite the first recess and spaced apart therefrom. In a preferred embodiment, the recesses are substantially annular, although other configurations for the recesses are also within the scope of the present invention. A primary conductive winding is disposed within the recess defined by the primary core, and a secondary conductive winding is disposed within the recess defined by the secondary core. The primary and secondary cores are arranged so as to form an air gap therebetween. The air gap permits relative rotation of the cores about a common axis of rotation.

The cores preferably have semi-toroidal configurations. In a preferred embodiment, the cores take the form of a plurality of individual ferrite core elements, disposed adjacent to each other in a substantially annular configuration. The individual core elements may be U-shaped or C-shaped. In one embodiment, each conductive winding is a multi-turn winding. In another embodiment, each conductive winding is a continuous, single turn annulus.

In the present invention, at least one of the primary and secondary windings comprises a fractional turn winding. A fractional turn winding is equal to a single turn winding multiplied by a factor N1/N2, where N1 and N2 are nonzero integers. The present invention is predicated in part on the realization that implementing fractional turn windings in the power coupling device described above allows for flexibility in the choice of voltages, both in and out.

The power coupling device of the present invention is adapted for coupling power to one or more rotating members at a plurality of voltage levels, the voltage levels having a magnitude equal to N1/N2 times a single turn voltage, and N1 and N2 being nonzero integers. If N1 is less than N2, each voltage level has a magnitude less than a single turn voltage, so that the fractional turn winding provides a low-power tap. If N1 is greater than N2, each voltage level has a magnitude greater than a single turn voltage, and the power coupling device functions as a step-up transformer. In one embodiment, the conductive windings are made of metallic foil.

In one embodiment, the primary core and the secondary core are situated concentrically with respect to each other about the common axis of rotation, and the air gap extends radially between the primary core and the secondary core. In this embodiment, the air gap has a substantially cylindrical configuration, and is also situated concentrically with respect to the common axis of rotation. In an alternate embodiment, the primary core and the secondary core are situated side by side, with the air gap extending axially therebetween. In this embodiment, the primary core and the secondary core have substantially the same dimensions.

In one embodiment, the power coupling device in accordance with the present invention includes conductive shields surrounding each core. The conductive shields are adapted to cancel out the oscillating magnetic fields that are formed just outside the gap between the primary and secondary cores, when a current is passed through the conductive windings. In one embodiment, the conductive shields are continuous, annular metallic shells having substantially semi-toroidal configurations.

In one embodiment, the power coupling device of the present invention includes a support structure for supporting the cores and the conductive windings. Preferably, the conductive shields discussed above are incorporated into the support structure.

BRIEF DESCRIPTION OF THE DRAWINGS

FIG. 2A illustrates an axial view of the power coupling device illustrated in FIG. 1. While a single turn winding is shown, for illustrative purposes, multiple turns can be used in other embodiments of the invention.

DETAILED DESCRIPTION

The present invention provides a method and system for coupling power to rotating systems. In particular, the use in the present invention of fractional turn windings allows for flexibility in the choice of input and output voltages. The power coupling device featured in the present invention also allows for the optimization of the current and voltage settings, so that optimal transfer efficiency can be achieved.

Figure 1:
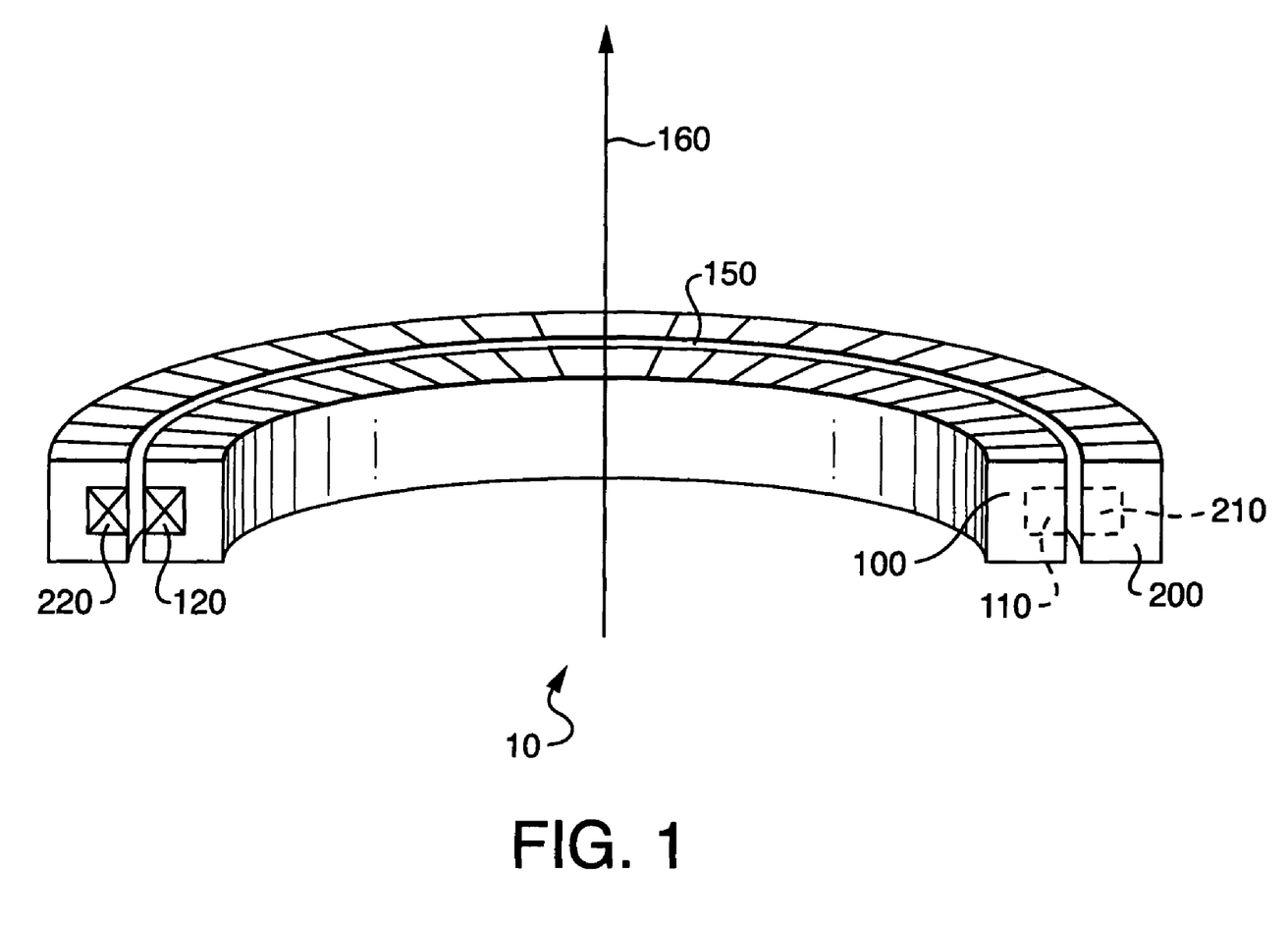
FIG. 1 illustrates a power coupling device in accordance with the present invention, including primary and secondary windings, and ferrite cores surrounding each winding.

FIG. 1 illustrates a power coupling device 10, constructed in accordance with one embodiment of the present invention. In FIG. 1, the power coupling device 10 is shown as cut in half, so that its constituent components (windings and cores) can be seen. The power coupling device 10 includes a primary magnetic core 100 and a secondary magnetic core 200. The primary magnetic core 100 defines a first recess or groove 110 (shown in dotted lines, for clarity), and surrounds a primary conductive winding 120. The secondary magnetic core 200 defines a second recess or groove 210 (also shown in dotted lines, for clarity), and surrounds a secondary conductive winding 220. In the illustrated embodiment, the primary core 100 and the secondary core 200 have a substantially semi-toroidal configuration, i.e. are shaped as half-toroidal shells. In this embodiment, the first 110 and second 210 recesses defined by the cores 100 and 200 are substantially annular. In the illustrated embodiment, the primary core is configured as the outer core, and the secondary core is configured as the inner core; however, this configuration is shown for illustrative purposes only, and other embodiments of the invention can position the primary core on the inside, and the secondary core on the outside.

As seen in FIG. 1, the secondary magnetic core 200 is disposed adjacent the primary magnetic core 100. The primary and secondary cores are arranged so as to form an air gap 150 therebetween. The second recess 210 is disposed opposite the first recess 110, and is spaced apart therefrom. The air gap 150 permits relative rotation of the cores about a common axis of rotation 160. In this way, at least one of the cores may be disposed on a rotating unit of a system, for example on the rotating gantry in a CT scanner, so as to rotate together with the rotating unit and deliver power to the unit. The cores are made of a magnetically permeable material, which may include, but is not limited to, ferrite, silicon iron, nickel ion alloy, stainless steel, and cobalt iron alloy.

Figure 2A:
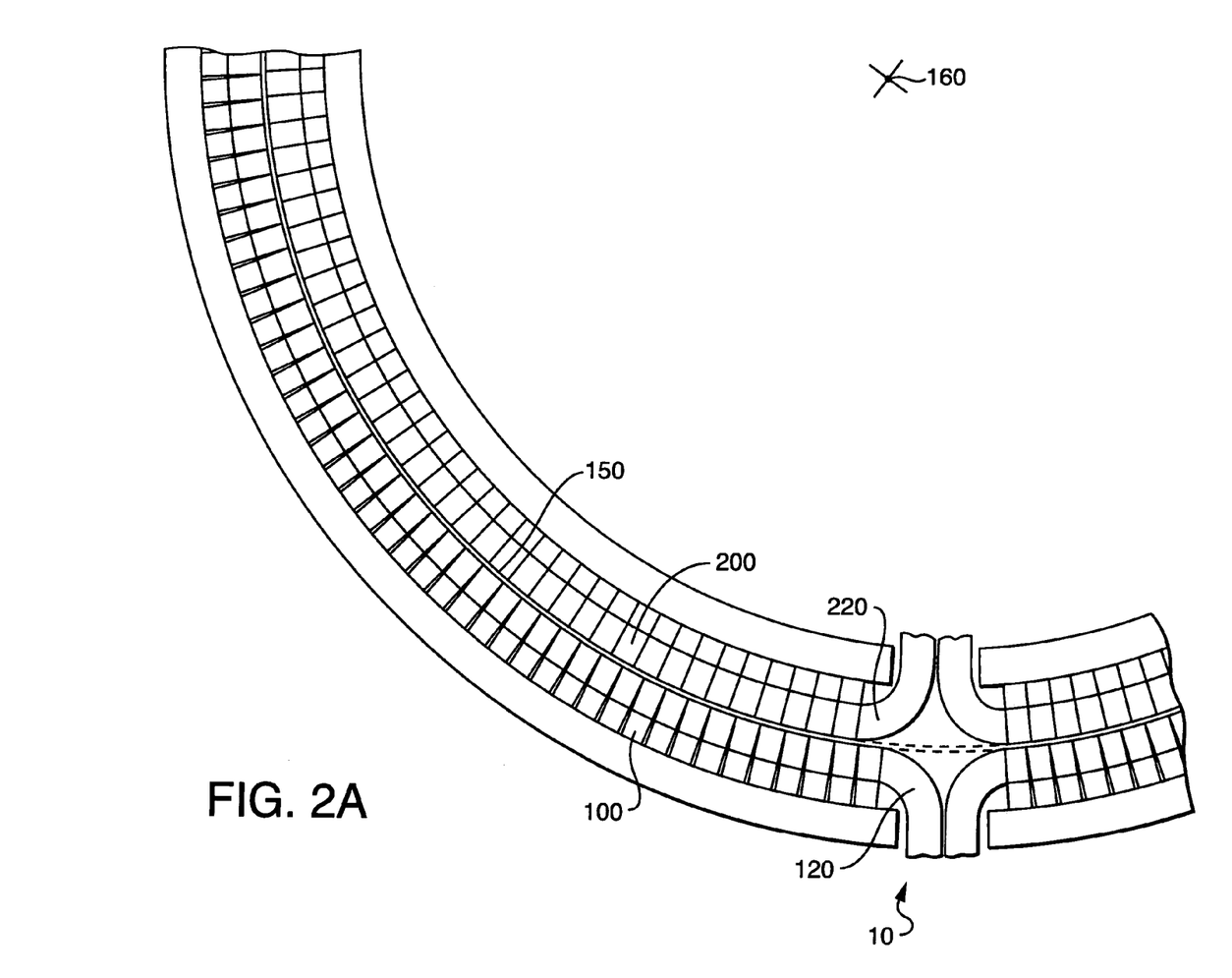
Figure 2B:
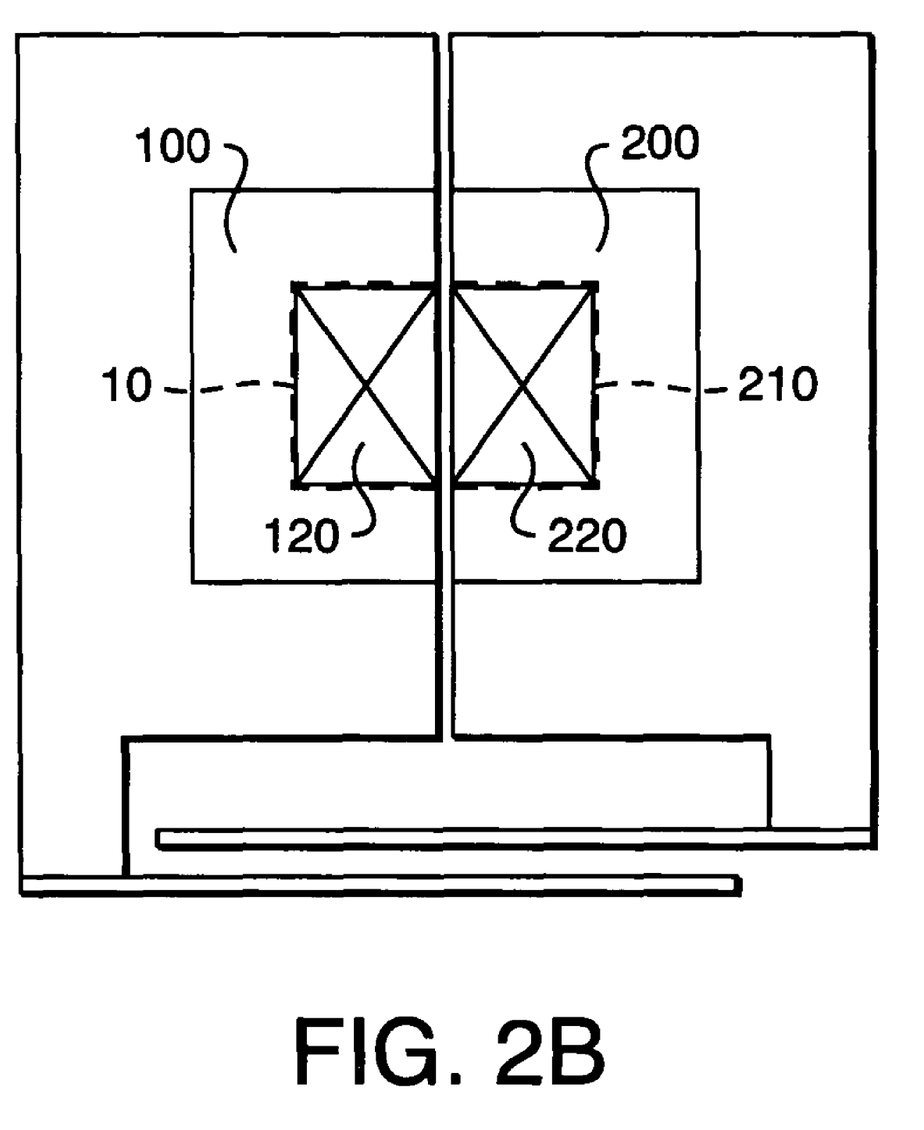
FIG. 2B shows a cross section of the power coupling device illustrated in FIGS. 1 and 2A.

FIG. 2A illustrates an axial view of the power coupling device 10 illustrated in FIG. 1, while FIG. 2B illustrates a cross section thereof. As seen from FIG. 2A, the coupling device 10 may be viewed, in its simplest form, as two circles 120 and 220 of a conductive element, surrounded by toroidal half-shells 100 and 200. As seen from FIG. 2B, the semi-toroidal cores 100 and 200 have substantially U-shaped cross-sections, although in other embodiments of the invention, the cores 100 and 200 may have cross-sections of different shapes, including but not limited to C-shaped cross-sections.

In the embodiment illustrated in FIGS. 1 and 2A-2B, the primary magnetic core 100 and the secondary magnetic core 200 are situated concentrically with respect to each other, with respect to their common axis of rotation 160. In this embodiment, the air gap 150 is situated concentrically with respect to the common axis of rotation 160, and extends radially between the primary core 100 and the secondary core 200. In an embodiment in which the magnetic cores 100 and 200 are shaped as half-toroidal shells, the air gap 150 has a substantially cylindrical configuration.

In the embodiments illustrated in FIGS. 1 and 2A-2B, the windings 120 and 220 are shown as single turns. This is purely for illustrative purposes only, and multiple turn windings are also within the scope of this invention.

In an alternative embodiment (not shown), the primary core 100 and the secondary core 200 are half-toroidal shells having substantially the same dimensions, both radially and axially, i.e. have the same radius, height, and width. In this embodiment, the primary core 100 (surrounding the primary conductive winding 120) and the secondary core 200 (surrounding the secondary conductive winding 220) are situated side by side, with the air gap 150 extending axially therebetween.

The power coupling device 10 may be analyzed using Faraday's Law $E=d\phi/dt$ and Ampere's Circuital Law $\int H \cdot dl = NI$. A current through the primary winding 120 creates magnetic field lines in the entire region, thereby electromagnetically inducing a current through the secondary winding 220. These field lines lie in radial planes, all of which pass through the axis 160 at the center of the conductive circles formed by the primary 120 and secondary 220 conductive windings.

In the embodiment illustrated in FIGS. 1 and 2A-2B, the primary core 100 and secondary core 200 are formed of a large number of individual ferrite core elements, and the primary and secondary windings are each formed as a single turn of a conductive element, surrounded by the ferrite cores.

This type of "reverse" topology is made possible because the magnetic field lines, created by the current in the primary winding, are in radial planes, so that the gaps between the many individual core elements forming each half-toroidal core, on a particular side (i.e. primary or secondary), will be parallel to the field lines, and will not affect them. Because no field lines cross the boundary between cores, the two (primary and secondary) half-toroidal cores can be viewed as continuous, even though they are actually formed of individual U-shaped (or C-shaped) core elements.

Preferably, the conductive element forming the windings is Litz wire. The term Litz wire (derived from the German word litzendraht meaning woven wire) is used to describe a wire constructed of individual filaments, bunched or braided together in a uniform pattern of twists and turns. The multi-strand configuration of Litz wires minimizes the power losses otherwise encountered in a solid conductor due to the "skin effect," i.e. the tendency of radio frequency current to be concentrated at the surface of the conductor.

When coupling power to rotating units of systems such as CT scanners, it is desirable to optimize the current and voltage, so as to achieve maximum power transfer efficiency. The power coupling device 10 illustrated in FIGS. 1 and 2A-2B allows for optimization of current and voltage, so that system losses are minimized and power transfer efficiency is maximized. The losses for the device 10 include core losses, shielding losses, and copper losses. For a given magnetic material forming the core, core losses are a non-linear function of the magnetization current. The magnetization current is the current that creates the magnetic field, since the induced emf is proportional to the rate of change of the magnetization current, under Faraday's law. In practice, the fields are so small that the core losses are nearly a linear function of the magnetization current. Copper losses are resistive, and are proportional to the square of the total current. The shielding losses are resistive, and proportional to the square of the magnetization current.

In addition to the magnetization current, the total current in the system includes load currents, which are equal to the emf divided by the load. Disregarding leakage flux, the load current in the secondary winding induces an equal and opposite current in the primary. Therefore, the load currents do not contribute to the field in the cores and consequently do not contribute to core losses. Core losses occur as a result of the energy that is required to build and/or reduce the magnetic fields within the magnetically permeable material that constitute the cores, and are thus proportional to the integral of the hysteresis loop for the material. When operating at lower voltages, core and shielding losses diminish, but copper losses increase, because of the need for higher currents. Conversely, when operating at higher voltages and lower currents, copper losses diminish, but the core and shielding losses increase.

Figure 3:
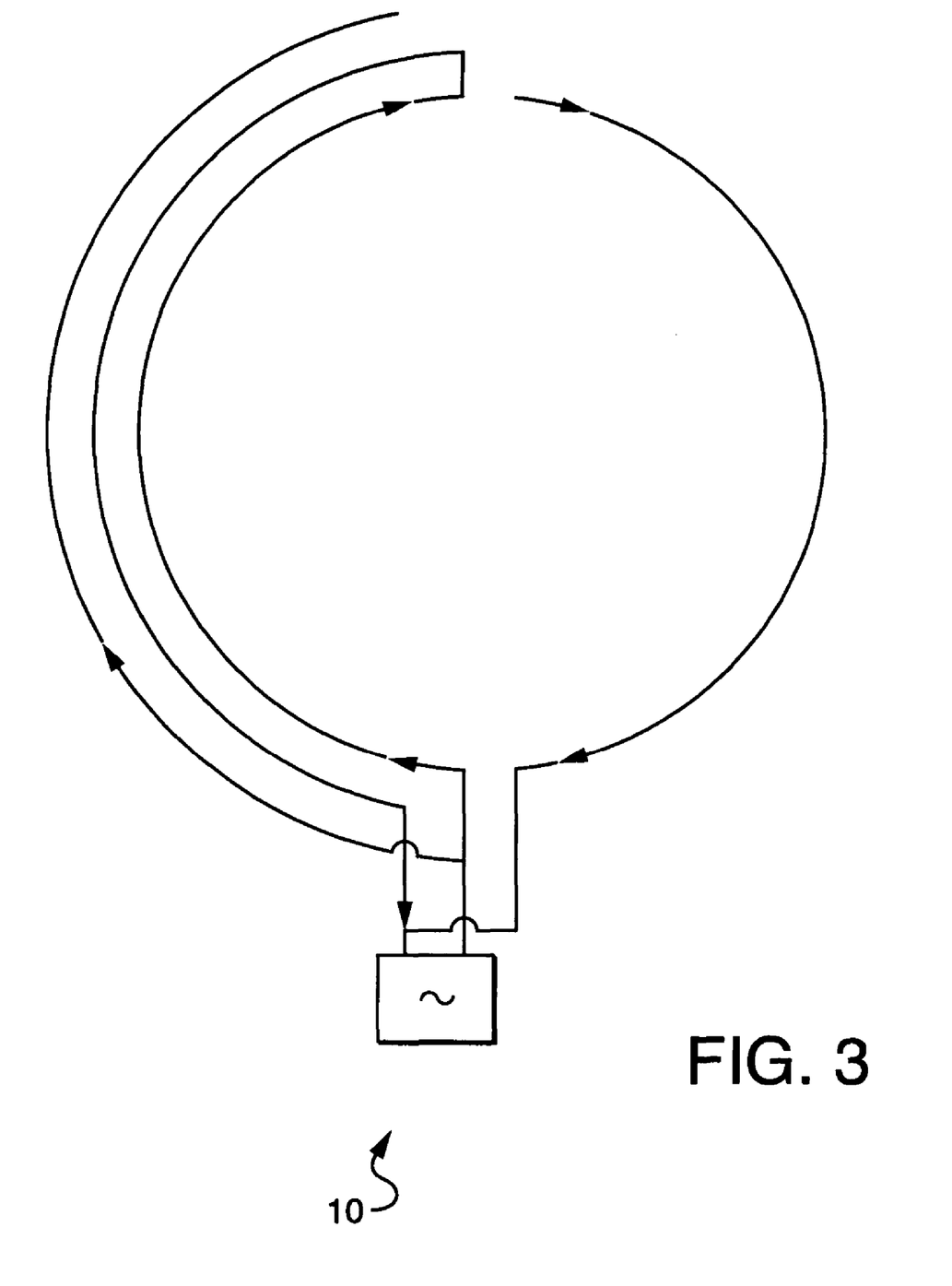
FIG. 3 illustrates a configuration for the power coupling device of FIG. 1, in which voltage is reduced and current is increased by using two half turns in the primary winding. With a particular choice of geometry, the power coupling device operates at an optimal efficiency, with an input of 450 volts and 356 amperes.

It is known that, for a given size (diameter), geometry, and material of a power transformer device, and for a given magnitude of the power to be transferred, there is an optimal current and voltage. Optimization equations known in the art may be used to calculate such optimal current and voltage, for a given configuration of the device 10. For example, for a power transfer of 80 kW with a commercially available 4215 UC core and a single turn winding having a diameter of 1.5 meter, the optimal current and voltage is 178 amperes (peak) and 900 Volts (peak) at 100 kHz. For these parameters, the calculated efficiency of energy transfer is better than 99.8%. While a current of 178 amperes is easily achieved economically, the same may not be said for a voltage level 900 Volts. High frequency power switching devices are typically limited to less than 600 volts. FIG. 3 discloses a configuration in which the coupling device 10 of the present invention can still work at its best efficiency with an input of 450 volts and 356 amperes, with no auxiliary transformer. This configuration achieves the same 99.8% calculated efficiency.

Unlike prior art rotary transformers, the power coupling device 10 of the present invention can accommodate fractional turn windings. Such fractional turn windings provide a solution for a common problem encountered by users and/or designers of CT scanning systems, namely the need to derive a plurality of different voltages, at a relatively low power, for devices on both the rotating gantry and the stationary gantry of the CT scanning system. For example, in a typical CT system, the high voltage power supply for the x-ray tube may require a voltage level of about 140 kV, the DAS (data acquisition system) may require a voltage level from between about −17 V to about +17 V, and electronic components such as the control circuitry and ADCs (analog-digital converters) may require voltage levels from about −15 V to about +15 V. The power requirements for a large CT system may be about 75 kW at 140 kV, and about 5 kW at several low voltages.

By using fractional turn windings, the power coupling device 10 of the present invention is adapted for coupling power to different components (both in the static gantry and in the rotating gantry) of a CT system or other rotatable system. Fractional turn windings may be used on either the primary winding, or the secondary winding, or both. The voltage from a fractional turn winding is equal to a single turn winding multiplied by a factor of N1/N2, where N1 and N2 are non-zero integers. Multiple voltages lower than the single turn voltage can be achieved by implementing fractional turn windings. If N1 is less than N2, each voltage level has a magnitude less than a single turn voltage, and the fractional turn winding provides a low-power tap, i.e. the power coupling device 10 functions as a step-down transformer.

The reverse topological configuration of the cores and windings, discussed in paragraph 33 above, allows for easy implementation of the fractional turn windings. For example, metallic foil (preferably copper foil) inserted into slots between individual core elements, in such a way that the two ends of the foil encompass a desired number of individual core elements (as required to effect the ratio N1/N2) provides a desired fractional turn winding for coupling to a voltage level that is N1/N2 times a single turn voltage.

Figure 4A:
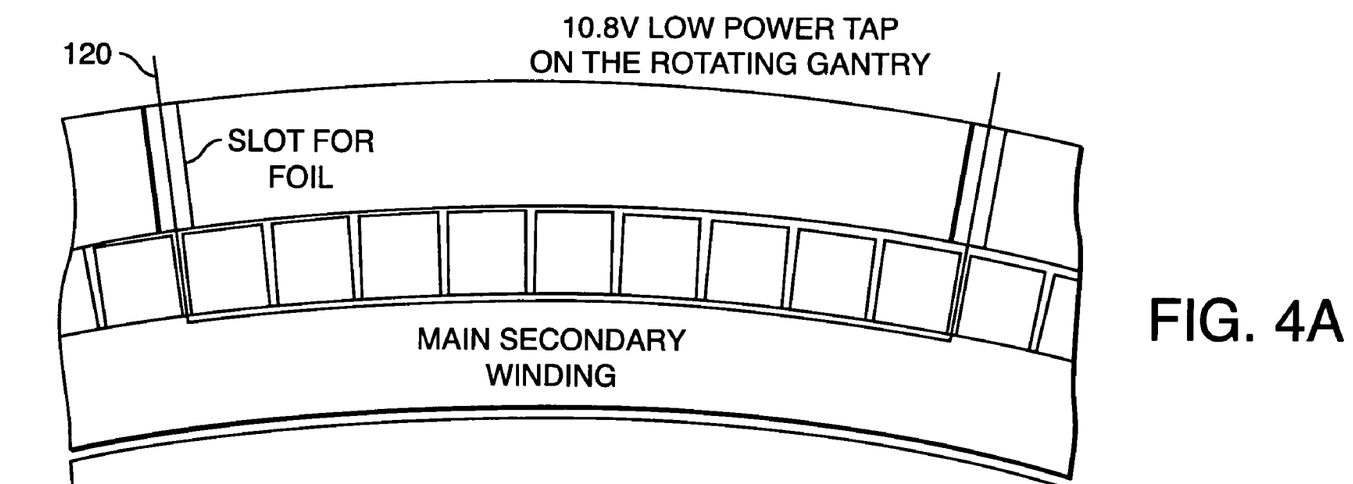
FIG. 4A illustrates a low power tap, formed of metallic foil, on a rotating gantry.
Figure 4B:
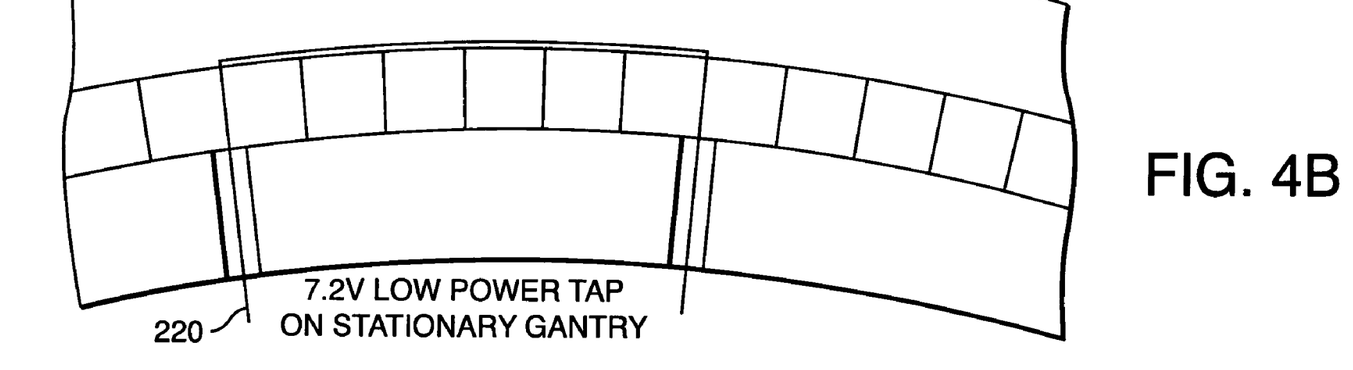
FIG. 4B illustrates a low power tap, formed of metallic foil, on a stationary gantry.

Low-power taps may be used in either the rotating component or the stationary component of the power coupling device 10. FIG. 4A illustrates a low power tap, formed of foil, on a rotating gantry of a CT system, while FIG. 4B illustrates a low-power tap, formed of foil, on a stationary gantry of a CT scanner. For a 900V secondary with 750 cores, each core will generate an emf of 1.2 V so 12 Volts would come from a 10-core winding. In the embodiment illustrated in FIG. 4A or 4B, the conductor for the winding may be a suitable foil (for example copper foil), or group of foils, depending on the current needed.

Figure 5:
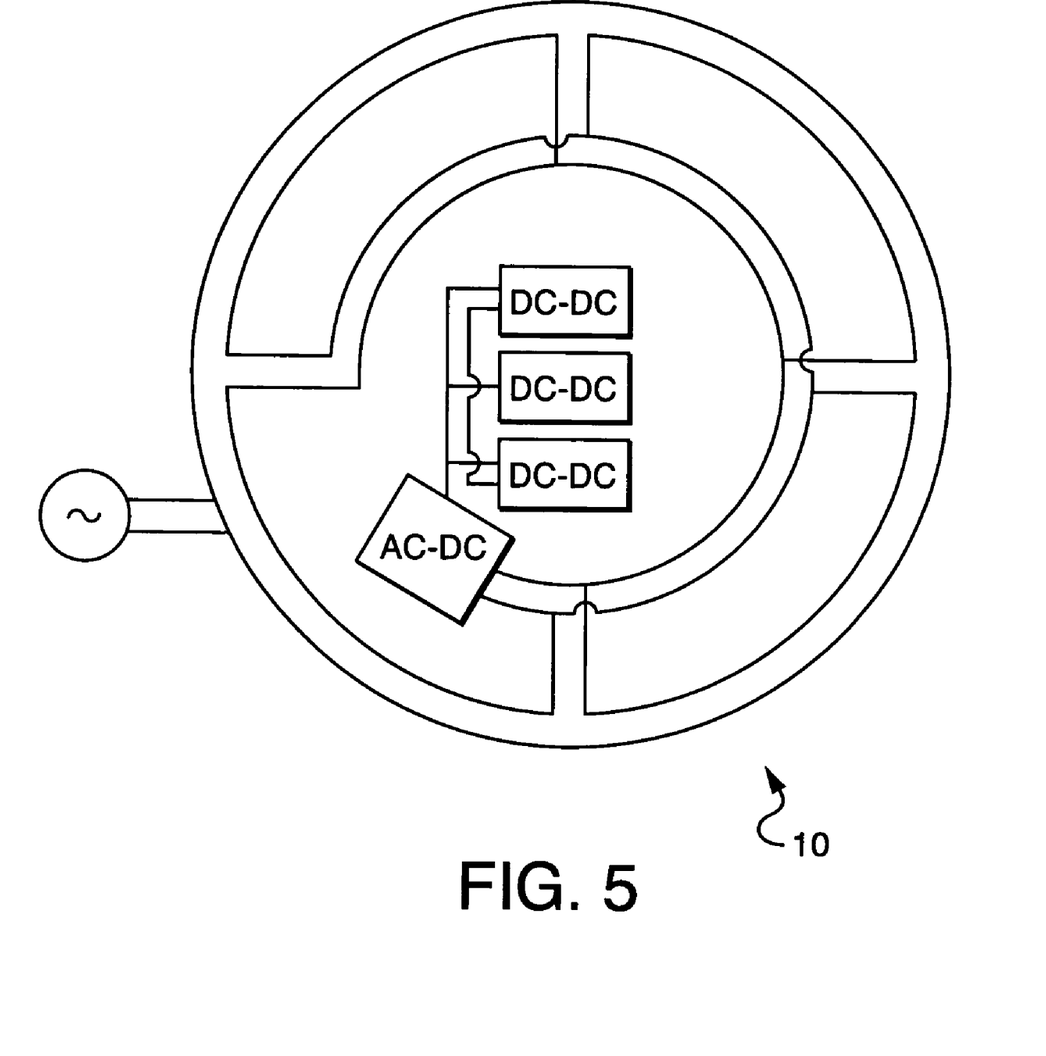
FIG. 5 illustrates a set of four one-quarter turn windings used to generate 225 volts from a 900-volt system.

A second approach for generating multiple voltages for different components of a rotary system would be to generate a single voltage, rectify this voltage, and use regulated DC to DC converters to obtain the multiple voltages. FIG. 5 illustrates a set of four one-quarter turn windings used to generate 225 volts from a 900-volt system. This is a result equivalent to twenty windings in parallel to generate 45 volts.

In some instances, it may be useful to obtain a higher voltage from the secondary winding, for example in order to drive the x-ray power source. To do this, the secondary winding of the inductive power coupling device can have two or more turns to achieve two or more times the voltage of a single turn at a corresponding decrease in current. The power impressed on the primary winding of the power coupling device can be servoed, for example in order to provide regulation for the high voltage power supply. The line regulation of the low voltage supplies must be sufficient to accept the variation of input power due to the high voltage servo.

Figure 6A:
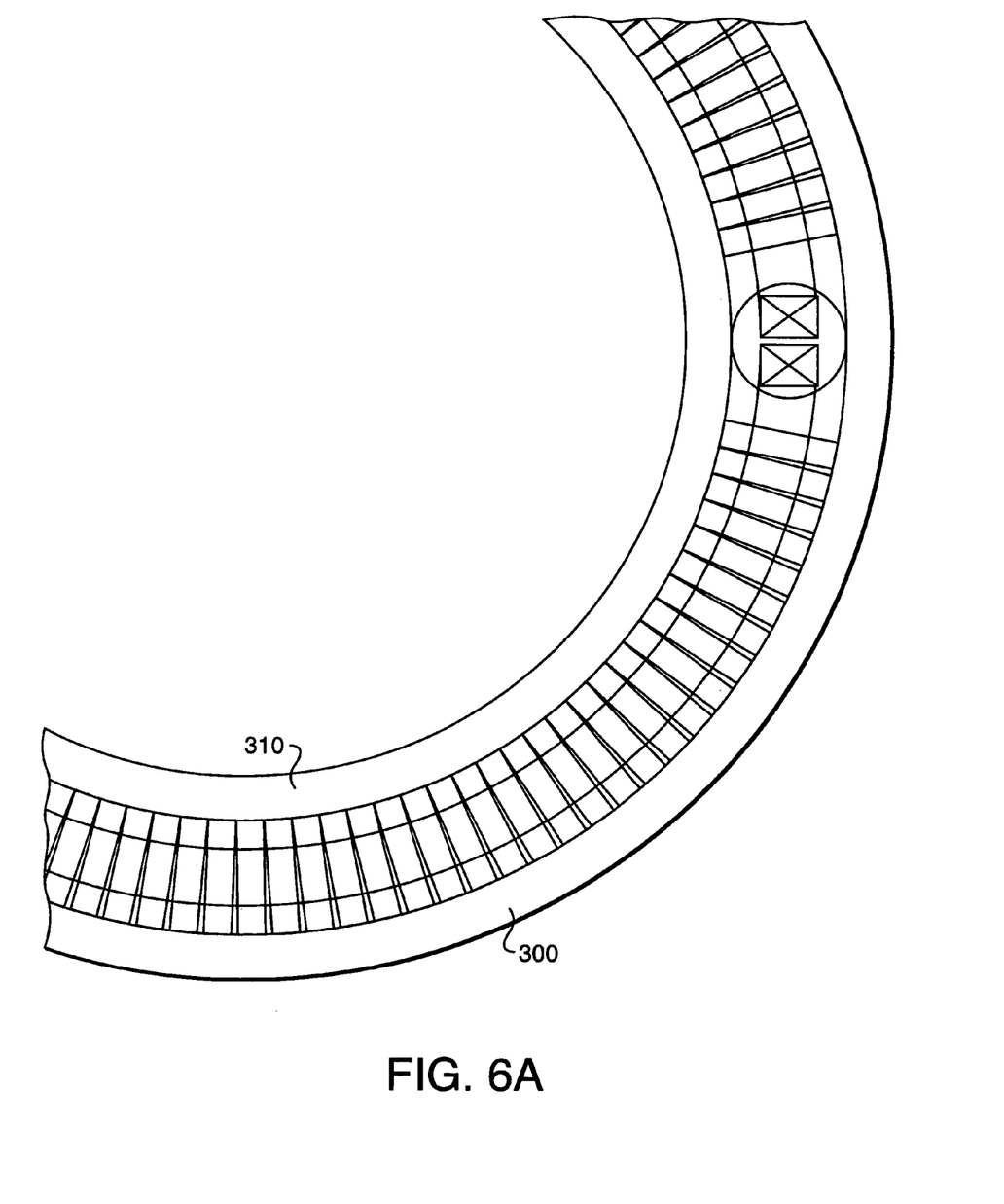
FIGS. 6A and 6B illustrate a power coupling device including metallic shields surrounding each core.
Figure 6B:
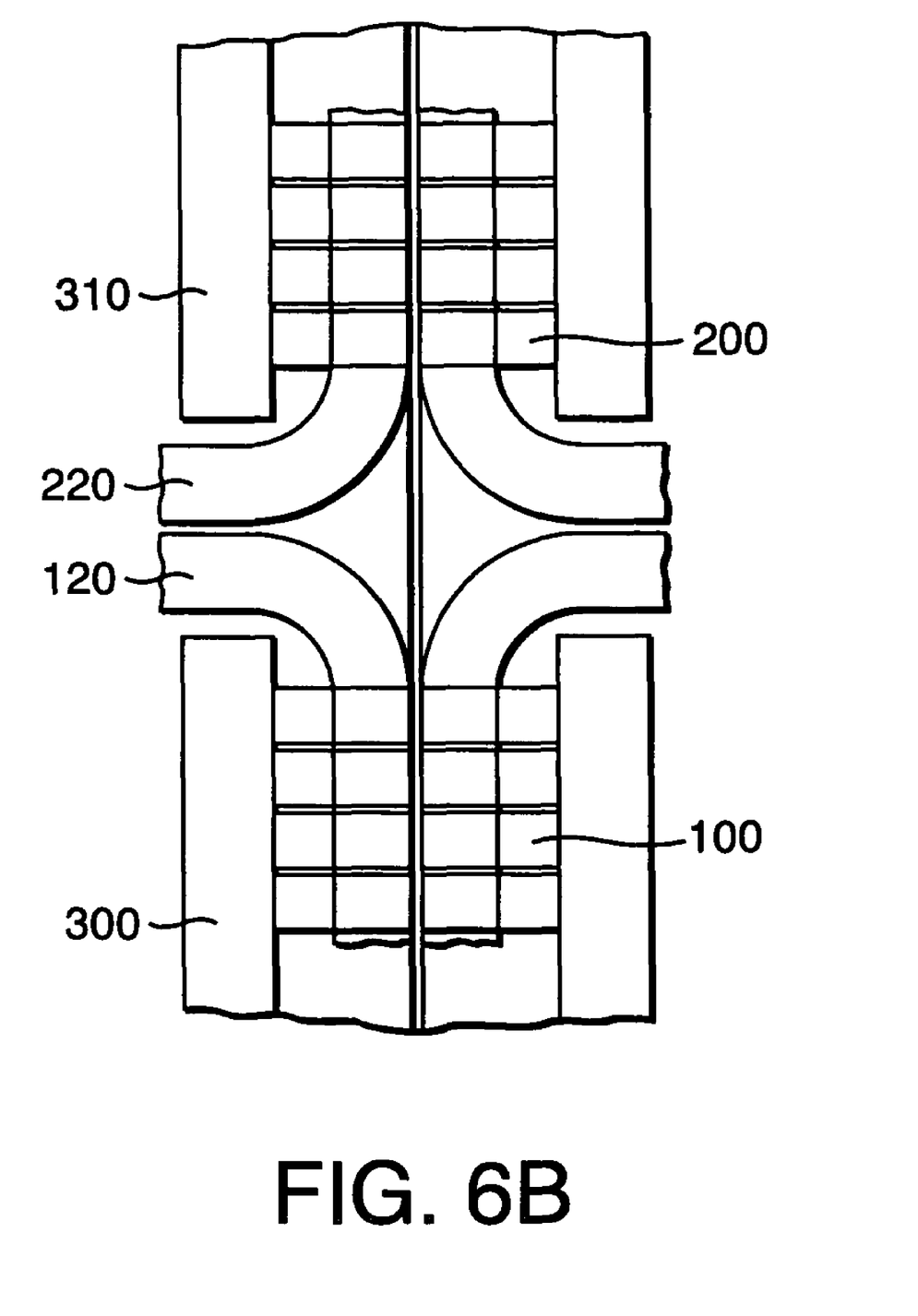
Figure 6C:
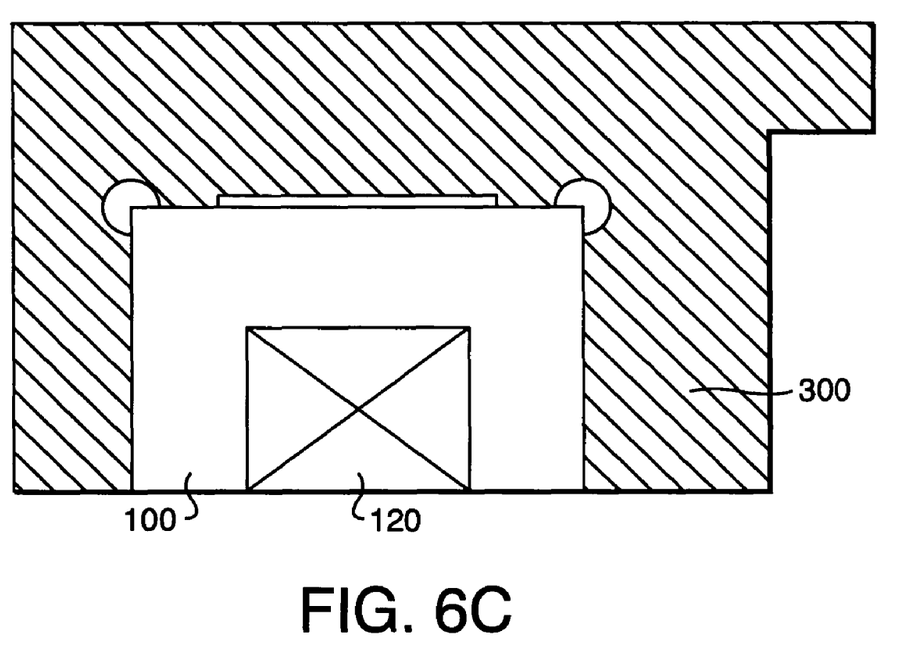
FIG. 6C illustrates a cross section of a power coupling device that includes a metallic shield.

In a preferred embodiment of the present invention, the primary and secondary magnetic cores are surrounded by conductive shields. FIGS. 6A and 6B illustrate one embodiment of the present invention in which each of the two magnetic cores are surrounded by aluminum shields 300 and 310, whereas FIG. 6C illustrates a cross sectional view of a power coupling device that includes aluminum shields. Preferably, the power coupling device of the present invention includes a support structure (not shown) for supporting the cores 100 and 200, and the conductive windings 120 and 220. In an embodiment of the invention including such a support structure, the shields are preferably incorporated into the support structure.

The conductive shields 300 and 310 serve to cancel the oscillating magnetic fields that are induced just outside the surface of the cores. The formation of these oscillating magnetic fields can be understood by applying appropriate boundary conditions to the surfaces of magnetic materials. As well known, two boundary conditions must be satisfied by the magnetic fields at the surface of a magnetic material: 1) the normal component of B must be constant across the boundary; and 2) the tangential component of H must be constant across the boundary. Application of these boundary conditions to the magnetic cores 100 and 200 shows the existence of an oscillating magnetic field just outside the surface of the cores. The flux lines of this field lie in radial planes, which all pass through the axis of rotation of the device. By surrounding the cores with shields having appropriate configurations, the oscillating magnetic fields will induce currents in these shields, and these induced currents will tend to cancel these oscillating magnetic fields. In a crude approximation, the cancellation will be a factor of about 37%, for each skin depth in the shielding.

As illustrated in FIGS. 6A and 6B, the conductive shields 300 and 310 are in the form of two continuous, circular half-toroidal shells, which surround each magnetic core 100 and 200. With shields having this type of configuration, an oscillating current distribution that exactly cancels the magnetic fields will flow in these conductive shells 300 and 310, due to the net current in the primary 120 and secondary 220 windings. These currents flow in circles which are coaxial with the gap between the half-toroids forming the shields 300 and 310. In this way, the gap between the two half-toroidal shields has no effect on the currents.

The net current in the primary 120 and secondary 220 windings is the magnetization current plus the portion of the secondary (load) current that is not cancelled by the primary load current. If there is enough conductive material in the shields 300 and 310, the oscillating magnetic field at the outside surfaces of the shields can be reduced by very large factors. For aluminum, by way of example, the skin depth at 100 kHz is 0.27 mm. In an embodiment in which the shields are part of a support structure for the power coupling device, it is practical to make the shields quite thick.

The shields 300 and 310 must be two continuous rings, covering the entire structure. If the structure of the shields 300 and 310 is formed in segments which are not connected to each other electrically, the oscillating magnetic field would create voltages across the gaps, instead of image currents, and there would be no shielding effect. To prevent leakage of radiation, the gap between the two halves of the shields 300 and 310 should be less than half the thickness of each shield at the gap.

The power coupling device of the present invention is useful for transmitting power at a plurality of voltage levels, in systems including at least one rotating unit, such as CT scanner. In systems including a static member, and a rotatable member coupled to the static member, the power coupling device of the present invention transmits power from the power source to either the static member or the rotatable member or both. For example, the static member may be the static gantry in the CT scanner, the rotatable member may be the rotatable gantry in the CT scanner, and have an x-ray source mounted to a distal end of the gantry.

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A power coupling device for coupling power to a rotating member, said power coupling device comprising:
    a. a primary magnetic core including a primary winding;
    b. a secondary magnetic core including a secondary winding;
    wherein said primary and secondary cores are arranged so as to form an air gap therebetween, said air gap permitting relative rotation of said cores about an axis of rotation while allowing power to be transferred across the air gap, and wherein at least one of said primary and said secondary windings comprises a fractional turn winding;
    c. conductive shielding configured as two continuous, circular half toroidal shells, each shell surrounding a respective one of the primary and secondary cores except for a portion adjacent the air gap, wherein when power is transferred across the air gap, oscillating magnetic fields will induce currents in the shielding, which induced currents tend to cancel the oscillating magnetic fields in a region outside the shielding.

2. A power coupling device in accordance with claim 1, wherein the conductive shielding is configured so as to create a substantially continuous conductive path around the axis of rotation for conducting the induced currents.

3. A power coupling device in accordance with claim 1, wherein the conductive shielding includes an annular shell providing an electrical path extending substantially continuously around the axis of rotation adjacent each core.

4. A power coupling device in accordance with claim 1, wherein the conductive shielding includes continuous, annular metallic shells having substantially semi-toroidal shapes configured to provide substantially conductive paths disposed adjacent the cores.

5. A power coupling device in accordance with claim 1, wherein the conductive shielding includes a conductive shell for each of the cores, each shell including at least a portion having a C-shaped cross section with a corresponding portion of a core disposed therein.

6. A power coupling device in accordance with claim 1, wherein each of the primary and secondary cores is configured as an annular conductive shell.

7. A power coupling device in accordance with claim 1, wherein the conductive shielding includes a continuous circular shell disposed about the axis of rotation surrounding each core with the exception of the air gap.

8. A power coupling device in accordance with claim 7, wherein the circular shell includes at least two segments, each segment being in the form of a continuous ring.

9. A power coupling device in accordance with claim 8, wherein the segments of each shell are electrically connected to one another.

10. A power coupling device in accordance with claim 1, wherein the shielding is of a predetermined thickness, and the air gap is less than one-half the predetermined thickness.

11. A power coupling device in accordance with claim 1, wherein the power transfer device forms a part of a CT scanner.

12. A power coupling device in accordance with claim 11, further including an X-ray tube arranged to rotate with the secondary magnetic core and receive power transferred across the air gap.

13. A rotary transformer system comprising:
    a. a primary transformer portion including a primary winding;
    b. a secondary transformer portion including a secondary winding;
    wherein the first and second transformer portions are configured so as to rotate relative to one another; and
    electrically conductive shielding as two continuous, circular half toroidal shells, each shell surrounding a respective one of the primary and secondary transformer portions except for a portion adjacent the air gap, wherein the shielding is arranged so as to substantially cancel oscillating magnetic fields generated when power is transferred between the primary transformer portion and the secondary transformer portion, and wherein at least one of said primary and said secondary windings comprises a fractional turn winding.

14. A rotary transformer system in accordance with claim 13, wherein the primary transformer portion and the secondary transformer portion each comprises a transformer core and an electrically conductive transformer winding.

15. A rotary transformer system in accordance with claim 13, wherein the electrically conductive shielding conducts current generated in response to the oscillating magnetic fields when power is transferred between the primary and secondary transformer portions so as to substantially cancel the oscillating fields in a region outside the shielding.

16. A rotary transformer system in accordance with claim 13, wherein the primary transformer portion is stationary and the secondary transformer portion rotates relative to the primary transformer.

17. A rotary transformer system in accordance with claim 13, wherein the primary and secondary transformer portions are spaced relative to one another so as to create an air gap therebetween.

18. A rotary transformer system in accordance with claim 13, wherein the conductive shielding is configured so as to create a substantially continuous conductive path for induced currents which in turn tend to cancel the oscillating magnetic fields in the region outside the shielding.

19. A rotary transformer system in accordance with claim 13, wherein the first and second transformer portions are configured so as to rotate relative to one another around an axis of rotation, and the conductive shielding includes at least one annular shell extending substantially continuously around the axis of rotation adjacent each of the transformer portions.

20. A rotary transformer system in accordance with claim 19, each annular shell has a substantially semi-toroidal shape disposed adjacent the corresponding transformer portion.

21. A rotary transformer system in accordance with claim 13, wherein the conductive shielding for each of the transformer portions includes at least a portion having a C-shaped cross section.

22. A rotary transformer system in accordance with claim 13, wherein the primary and secondary transformer portions are spaced from one another so as to create an air gap therebetween, and the conductive shielding includes a continuous circular shell surrounding each transformer portion with the exception of the air gap.

23. A rotary transformer system in accordance with claim 22, wherein each shell is a circular shell surrounding a respective transformer portion with the exception of the air gap, each shell including at least two segments, and each segment being in the form of a continuous ring.

24. A rotary transformer system in accordance with claim 23, wherein the segments of each shell are electrically connected to one another.

25. A rotary transformer system in accordance with claim 13, wherein the shielding is of a predetermined thickness, and the air gap is less than one-half the predetermined thickness.

26. A rotary transformer system in accordance with claim 13, wherein the rotary transformer system forms a part of a CT scanner.

27. A rotary transformer system in accordance with claim 26, further including an X-ray tube arranged to rotate with the secondary transformer portion so as to receive power transferred between the primary transformer portion and the secondary transformer portion.

* * * * *

UNITED STATES PATENT AND TRADEMARK OFFICE
CERTIFICATE OF CORRECTION

| | | |
|---|---|---|
| PATENT NO. | : 7,868,723 B2 | Page 1 of 1 |
| APPLICATION NO. | : 10/787270 | |
| DATED | : January 11, 2011 | |
| INVENTOR(S) | : John Dobbs | |

It is certified that error appears in the above-identified patent and that said Letters Patent is hereby corrected as shown below:

In the Claims

Column 8, line 51, please delete "including" and insert --...and...--;

Column 8, line 52, please delete "including" and insert --...and...--;

Column 8, line 57, please delete ", and";

Column 8, line 58, please delete "wherein at least one of said primary and said secondary wind-";

Column 8, line 59, please delete "ings comprises a fractional turn winding";

Column 8, line 60, please delete "configured as" and insert --...including at least...--;

Column 8, line 61, please delete "half";

Column 8, line 61, please delete "shells" and insert --...sections...--;

Column 8, line 61, please delete "shell surrounding" and insert --...section being positioned so as to be adjacent...--;

Column 9, line 57, please delete ", and wherein at least";

Column 9, line 58, please delete "one of said primary and said secondary windings com-";

Column 9, line 59, please delete "prises a fractional turn winding".

Signed and Sealed this
Thirty-first Day of December, 2013

Margaret A. Focarino
*Commissioner for Patents of the United States Patent and Trademark Office*